US012697163B2

(12) United States Patent
Zhong et al.

(10) Patent No.: US 12,697,163 B2
(45) Date of Patent: Aug. 4, 2026

(54) PULSE MONITORING METHOD, APPARATUS AND DEVICE, AND STORAGE MEDIUM

(71) Applicant: HANGZHOU WKNIFE MEDICAL TECHNOLOGY CO., LTD., Hangzhou (CN)

(72) Inventors: Xinghua Zhong, Hangzhou (CN); Long Wang, Hangzhou (CN); Ke Yang, Hangzhou (CN)

(73) Assignee: HANGZHOU WKNIFE MEDICAL TECHNOLOGY CO., LTD., Hangzhou (CN)

( * ) Notice: Subject to any disclaimer, the term of this patent is extended or adjusted under 35 U.S.C. 154(b) by 247 days.

(21) Appl. No.: 18/587,394

(22) Filed: Feb. 26, 2024

(65) Prior Publication Data

US 2024/0189017 A1     Jun. 13, 2024

Related U.S. Application Data

(63) Continuation of application No. PCT/CN2022/115891, filed on Aug. 30, 2022.

(30) Foreign Application Priority Data

Sep. 1, 2021     (CN) .......................... 202111020857.6

(51) Int. Cl.
*A61B 18/14*          (2006.01)
*A61B 18/00*          (2006.01)

(52) U.S. Cl.
CPC .... *A61B 18/14* (2013.01); *A61B 2018/00577* (2013.01); *A61B 2018/00642* (2013.01);
(Continued)

(58) Field of Classification Search
CPC .......... A61B 18/14; A61B 2018/00577; A61B 2018/00642; A61B 2018/00767;
(Continued)

(56) References Cited

U.S. PATENT DOCUMENTS

| | | | |
|---|---|---|---|
| 11,925,405 B2 * | 3/2024 | Davalos .............. | A61B 5/4836 |
| 2016/0066977 A1 | 3/2016 | Neal et al. | |
| 2020/0289185 A1 | 9/2020 | Forsyth et al. | |

FOREIGN PATENT DOCUMENTS

| | | |
|---|---|---|
| CN | 109124760 A | 1/2019 |
| CN | 109157280 A | 1/2019 |

(Continued)

OTHER PUBLICATIONS

Extended European Search Report issued in counterpart European Patent Application No. 22863466.3, dated Jan. 14, 2025.

(Continued)

*Primary Examiner* — Beverly M Flanagan
(74) *Attorney, Agent, or Firm* — Westbridge IP LLC

(57) ABSTRACT

A pulse monitoring method includes: applying a first pulse sequence and a second pulse sequence to target biological tissue; where a voltage of the second pulse sequence is smaller than a voltage of the first pulse sequence, and the first pulse sequence is used to ablate the target biological tissue; obtaining a feedback signal after the second pulse sequence is applied to the target biological tissue; determining, according to the feedback signal, whether a termination condition for the first pulse sequence is met; stopping applying the first pulse sequence when it is determined that the termination condition for the first pulse sequence is met.

14 Claims, 4 Drawing Sheets

(52) U.S. Cl.
  CPC ............... *A61B 2018/00767* (2013.01); *A61B 2018/00827* (2013.01); *A61B 2018/00875* (2013.01); *A61B 2018/00892* (2013.01); *A61B 2018/00898* (2013.01)

(58) Field of Classification Search
  CPC ........... A61B 2018/00827; A61B 2018/00875; A61B 2018/00892; A61B 2018/00898; A61B 2018/00666; A61B 2018/00779; A61B 2018/00702
  USPC .......................................................... 606/41
  See application file for complete search history.

(56)              References Cited

FOREIGN PATENT DOCUMENTS

| | | | |
|---|---|---|---|
| CN | 112540221 | A | 3/2021 |
| CN | 112842516 | A | 5/2021 |
| CN | 113648053 | A | 11/2021 |
| EP | 1769762 | A1 | 4/2007 |
| WO | 2020061192 | A1 | 3/2020 |

OTHER PUBLICATIONS

First Office Action issued in counterpart Chinese Patent Application No. 202111020857.6, dated Mar. 27, 2025.

Notice of Reasons for Refusal issued in counterpart Japanese Patent Application No. JP 2024-514033, dated Jan. 21, 2025.

International Search Report issued in corresponding PCT Application No. PCT/CN2022/115891, dated Nov. 28, 2022.

Request for the Submission of an Opinion issued in counterpart Korean Patent Application No. KR 10-2024-7010623, dated May 21, 2026.

* cited by examiner

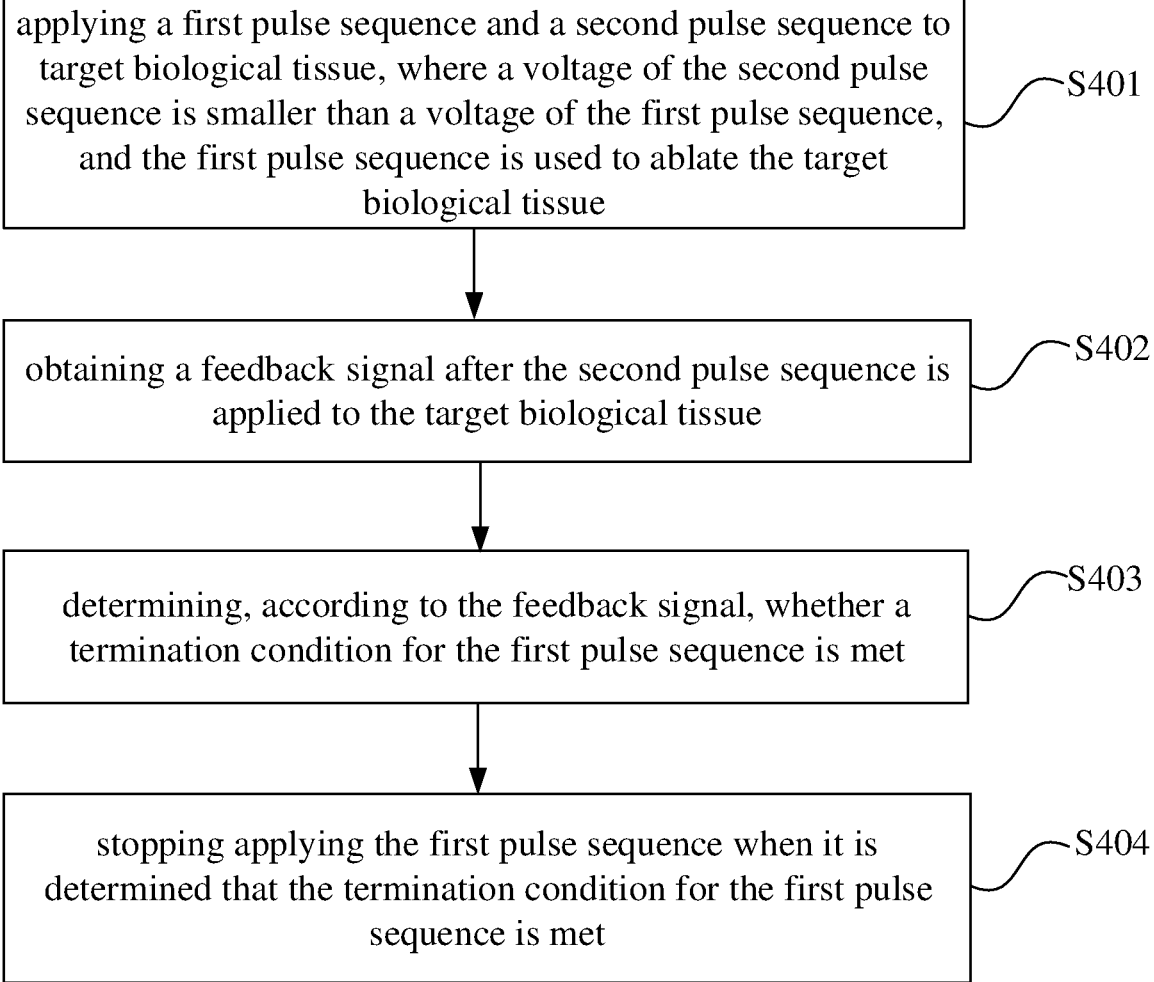

applying a first pulse sequence and a second pulse sequence to target biological tissue, where a voltage of the second pulse sequence is smaller than a voltage of the first pulse sequence, and the first pulse sequence is used to ablate the target biological tissue          S401 obtaining a feedback signal after the second pulse sequence is applied to the target biological tissue          S402 determining, according to the feedback signal, whether a termination condition for the first pulse sequence is met          S403 stopping applying the first pulse sequence when it is determined that the termination condition for the first pulse sequence is met          S404

Fig. 4

PULSE MONITORING METHOD, APPARATUS AND DEVICE, AND STORAGE MEDIUM

CROSS-REFERENCE TO RELATED APPLICATIONS

This application is a continuation of PCT Application No. PCT/CN2022/115891, filed on Aug. 30, 2022, which claims priority to Chinese Patent Application No. 202111020857.6, filed on Sep. 1, 2021. All of the aforementioned applications are incorporated herein by reference in their entireties.

TECHNICAL FIELD

The present application relates to the field of medical device technologies, in particular to a pulse monitoring method, a pulse monitoring apparatus, a pulse monitoring device, and a storage medium.

BACKGROUND

Pulse ablation is an emerging biological tissue ablation technology that is applicable to the treatment of clinical diseases such as tumor ablation, cardiac tissue ablation, and hyperplasia tissue ablation.

Currently, during a pulse ablation process, real-time monitoring and evaluation of ablation effects of a target biological tissue have not been considered. Consequently, it is unable to guide the pulse ablation process based on the state changes of the target biological tissue.

SUMMARY

In a first aspect, embodiments of the present application provide a pulse monitoring method, including:

applying a first pulse sequence and a second pulse sequence to target biological tissue; where a voltage of the second pulse sequence is smaller than a voltage of the first pulse sequence, and the first pulse sequence is used to ablate the target biological tissue;

obtaining a feedback signal after the second pulse sequence is applied to the target biological tissue;

determining, according to the feedback signal, whether a termination condition for the first pulse sequence is met;

stopping applying the first pulse sequence when it is determined that the termination condition for the first pulse sequence is met.

In a possible embodiment of the present application, applying the first pulse sequence and the second pulse sequence to the target biological tissue includes: applying a first set quantity of first pulse sequences and a second set quantity of second pulse sequences to the target biological tissue sequentially and alternately.

In a possible embodiment of the present application, the first pulse sequence includes at least one type of pulse and the second pulse sequence includes at least one type of pulse.

In a possible embodiment of the present application, the first pulse sequence includes a nanosecond pulse, or the first pulse sequence includes a nanosecond pulse and a microsecond pulse. The second pulse sequence includes a microsecond pulse.

In a possible embodiment of the present application, the voltage of the first pulse sequence is greater than 500V and not greater than 15 kV; and/or, the voltage of the second pulse sequence is not greater than 500V.

In a possible embodiment of the present application, obtaining the feedback signal after the second pulse sequence is applied to the target biological tissue includes: obtaining a real-time voltage and a real-time current of a feedback circuit corresponding to the target biological tissue after the second pulse sequence is applied to the target biological tissue;

determining whether the termination condition for the first pulse sequence is met according to the feedback signal includes:

determining, according to the real-time voltage and real-time current of the feedback circuit, a real-time impedance value of the target biological tissue;

determining whether the real-time impedance value is less than a set impedance value; or, displaying the real-time impedance value and determining whether a termination instruction for the first pulse sequence is received; and stopping applying the first pulse sequence when it is determined that the termination condition for the first pulse sequence is met includes:

stopping applying the first pulse sequence when it is determined that the real-time impedance value is less than the set impedance value; or, stopping applying the first pulse sequence when it is determined that the termination instruction for the first pulse sequence is received.

In a possible embodiment of the present application, displaying the real-time impedance value includes at least one of the following:

displaying a real-time impedance value curve, where the real-time impedance value curve includes at least two real-time impedance values in a set time period; or, displaying the real-time impedance value and corresponding biological indicator information of the target biological tissue, where the biological indicator information includes at least one of the following: heart rate, blood pressure or blood oxygen concentration.

In a possible embodiment of the present application, displaying the real-time impedance value and determining whether the termination instruction for the first pulse sequence is received includes:

issuing an alarm prompt when the biological indicator information of the target biological tissue is greater than a set threshold, where the alarm prompt includes emitting an alarm sound and/or outputting alarm information;

outputting the termination instruction for the first pulse sequence in response to receiving the alarm information.

In a second aspect, embodiments of the present application provide a pulse monitoring apparatus, including:

a pulse applying module, configured to apply a first pulse sequence and a second pulse sequence to target biological tissue; where a voltage of the second pulse sequence is smaller than a voltage of the first pulse sequence, and the first pulse sequence is used to ablate the target biological tissue;

an obtaining module, configured to obtain a feedback signal after the second pulse sequence is applied to the target biological tissue;

a processing module, configured to determine, according to the feedback signal, whether a termination condition for the first pulse sequence is met, and stop applying the first pulse sequence when it is determined that the termination condition for the first pulse sequence is met.

In a third aspect, embodiments of the present application provide a pulse monitoring device, including a pulse generating circuit, a control unit and a monitoring unit. The control unit is communicatively connected to the pulse generating circuit, and configured to control the pulse generating circuit to apply a first pulse sequence and a second pulse sequence to target biological tissue. A voltage of the second pulse sequence is smaller than a voltage of the first pulse sequence, and the first pulse sequence is used to ablate the target biological tissue. The control unit is further configured to determine, according to a feedback signal forwarded by the monitoring unit, whether a termination condition for the first pulse sequence is met, and output a termination instruction for the first pulse sequence to the pulse generating circuit when it is determined that the termination condition for the first pulse sequence is met. The monitoring unit is communicatively connected to the control unit, and configured to obtain the feedback signal after the second pulse sequence is applied to the target biological tissue, and output the feedback signal to the control unit.

In a possible embodiment of the present application, the pulse generating circuit includes a first pulse generating circuit for outputting the first pulse sequence and a second pulse generating circuit for outputting the second pulse sequence. The first pulse generating circuit and the second pulse generating circuit are integrated on a same circuit board.

In a possible embodiment of the present application, the first pulse generating circuit includes at least one level of first pulse generating units electrically connected sequentially. Each first pulse generating unit is electrically connected to the control unit, and configured to be turned on under control of the control unit and apply the first pulse sequence to the target biological tissue.

In a possible embodiment of the present application, each of the at least one level of first pulse generating units includes a first capacitor, a first switching device and a first diode, a first terminal of the first capacitor is electrically connected to a first terminal of the first switching device, a positive electrode and a negative electrode of the first diode are electrically connected to a second terminal of the first capacitor and a second terminal of the first switching device respectively, and a control terminal of the first switching device is electrically connected to the control unit.

In a possible embodiment of the present application, the first pulse generating circuit further includes at least one second diode; a first terminal of a first capacitor in a first level of first pulse generating unit in the at least one level of first pulse generating units is electrically connected to a first power source through the at least one second diode.

In a possible embodiment of the present application, the first pulse generating circuit further includes at least one third diode, an anode and a cathode of the third diode are electrically connected to two adjacent first pulse generating units respectively.

In a possible embodiment of the present application, the second pulse generating circuit includes at least one level of second pulse generating units electrically connected sequentially. Each second pulse generating unit is electrically connected to the control unit and configured to be turned on under control of the control unit and apply the second pulse sequence to the target biological tissue.

In a possible embodiment of the present application, the second pulse generating unit includes a second capacitor, a second switching device and a fourth diode; a first terminal of the second capacitor is electrically connected to a first terminal of the second switching device, a positive electrode and a negative electrode of the fourth diode are electrically connected to a second terminal of the second capacitor and a second terminal of the second switching device respectively, and a control terminal of the second switching device is electrically connected to the control unit.

In a possible embodiment of the present application, the pulse monitoring device further includes a display unit communicatively connected to the control unit, where the display unit is configured to display at least one of a real-time impedance value, a real-time impedance value curve or biological indicator information.

In a possible embodiment of the present application, the pulse monitoring device further includes an alarm unit communicatively connected to the control unit, where the alarm unit is configured to issue an alarm prompt when the biological indicator information of the target biological tissue is greater than a set threshold.

In a fifth aspect, embodiments of the present application provide a computer-readable storage medium having a computer program stored thereon, the computer program implementing, when executed by a pulse monitoring device, the pulse monitoring method in the first aspect.

The additional aspects and advantages of the present disclosure will be given or may become apparent in the following description, or may be understood through the implementation of the present application.

BRIEF DESCRIPTION OF THE DRAWINGS

The above and/or additional aspects as well as advantages of the present application will become apparent and are easily understood in the following description with reference to the following drawings. In these drawings:

FIG. 4 is a schematic flow chart of a pulse monitoring method according to the embodiments of the present application;

DETAILED DESCRIPTION OF THE EMBODIMENTS

Figure 1:
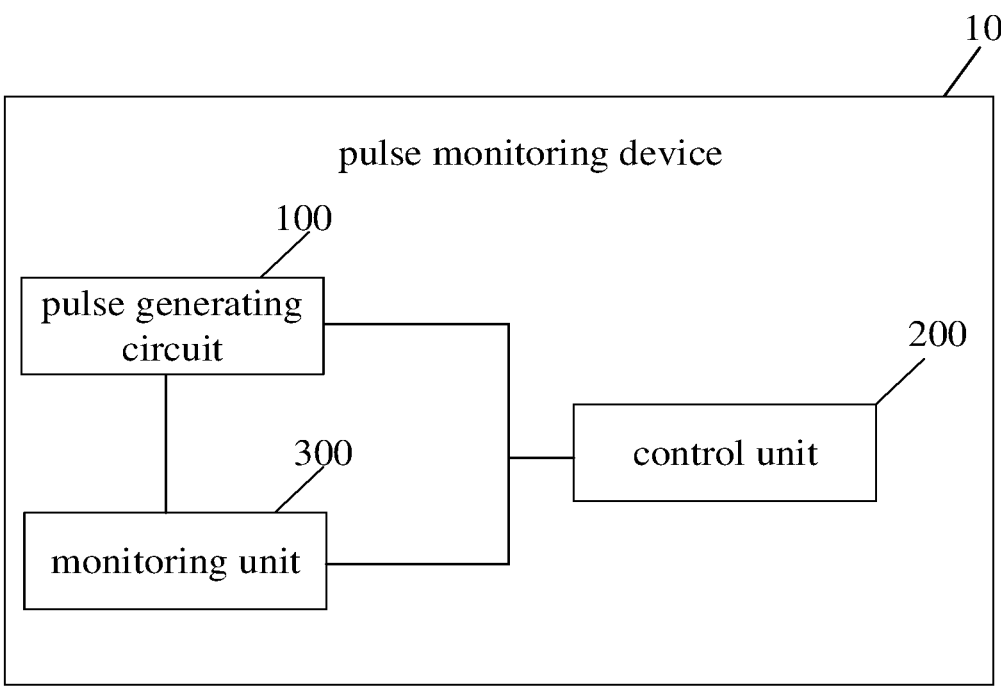
FIG. 1 is a schematic structural diagram of a pulse monitoring device according to the embodiments of the present application.

The present application will be described hereinafter in conjunction with the embodiments and the drawings. Identical or similar reference numbers in the drawings represent an identical or similar element or elements having an identical or similar function. In addition, the detailed description about any known technology will be omitted when it is unnecessary to the features in the present application. The following embodiments are for illustrative purposes only, but shall not be used to limit the scope of the present application.

As can be appreciated by a person skilled in the art, unless otherwise defined, all terms (including technical and scientific terms) used herein have the same meaning as commonly understood by one of ordinary skill in the art to which the present application is a part. Terms, such as those defined in commonly used dictionaries, should be interpreted as having a meaning that is consistent with their meaning in the context of the relevant art and will not be interpreted in an idealized or overly formal sense, unless expressly so defined herein.

As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. In the case that one element is connected or coupled to another element, it may be directly connected or coupled to the other element, or an intermediate element may be arranged therebetween. At this time, the element may be connected or coupled to the other element in a wireless or wired manner. In addition, the expression "and/or" is used to indicate the existence of all or any one of one or more of listed items, or combinations thereof.

Through research, it has been found that, in a conventional pulse ablation process, real-time monitoring and evaluation of the pulse ablation effects have not been considered. Consequently, it is unable to obtain the changes in biological tissue during the ablation process, and thus there is no basis for precisely guiding the pulse ablation progress.

It has been further found through research that most of the conventional pulse ablation technologies only focus on lesion location, and there is no disclosed method or technology that can monitor the pulse ablation process in real time. Moreover, in order to realize a monitoring function for the existing pulse generating apparatus, other monitoring devices or independent modules need to be equipped. Therefore, further exploration is needed to achieve monitoring of pulse ablation.

The present application provides a pulse monitoring method, a pulse monitoring apparatus, a pulse monitoring device, and a storage medium, so as to solve the above technical problems in the prior art.

The technical solutions of the present application and how the technical solutions of the present application solve the above technical problems will be described in detail below with reference to specific embodiments.

The embodiments of the present application provide a pulse monitoring device 10. As shown in FIG. 1, the pulse monitoring device 10 includes: a pulse generating circuit 100, a control unit 200 and a monitoring unit 300.

The control unit 200 is communicatively connected to the pulse generating circuit 100, and configured to control the pulse generating circuit 100 to apply a first pulse sequence and a second pulse sequence to target biological tissue. A voltage of the second pulse sequence is smaller than a voltage of the first pulse sequence, and the first pulse sequence is used to ablate the target biological tissue. The control unit is further configured to determine, according to a feedback signal forwarded by the monitoring unit 300, whether a termination condition for the first pulse sequence is met, and output a termination instruction for the first pulse sequence to the pulse generating circuit 100 when it is determined that the termination condition for the first pulse sequence is met.

The monitoring unit 300 is communicatively connected to the control unit 200, and configured to obtain the feedback signal after the second pulse sequence is applied to the target biological tissue, and output the feedback signal to the control unit 200.

The pulse generation circuit 100 of the pulse monitoring device 10 in the embodiments of the present application may apply the first pulse sequence and the second pulse sequence to the target biological tissue under the control of the control unit 200, and the control unit 200 determines according to the feedback signal from the monitoring unit 300 whether the termination condition for the first pulse sequence is met. That is, during a pulse ablation process, the control unit 200 may determine an ablation status of the target biological tissue based on the feedback signal, so as to monitor the ablation status of the target biological tissue during the pulse ablation process in real time.

The control unit 200 in the embodiments of the present application can guide the pulse ablation process according to the state change of the biological tissue. After determining that the pulse ablation effect is achieved, the control unit 200 outputs a termination instruction for the first pulse sequence, so that the control unit 200 controls the pulse generation circuit 100 to stop outputting the first pulse sequence for biological tissue ablation, thereby to guide the pulse ablation process according to changes in biological tissue.

Through the pulse monitoring device 10 in the embodiments of the present application, it realizes that two functions of pulse ablation and monitoring are integrated into one device, and thereby it does not need to be equipped with other monitoring devices or independent modules, making it convenient to use and operate.

Optionally, the target biological tissue includes a portion of a human body to be ablated.

Figure 2:
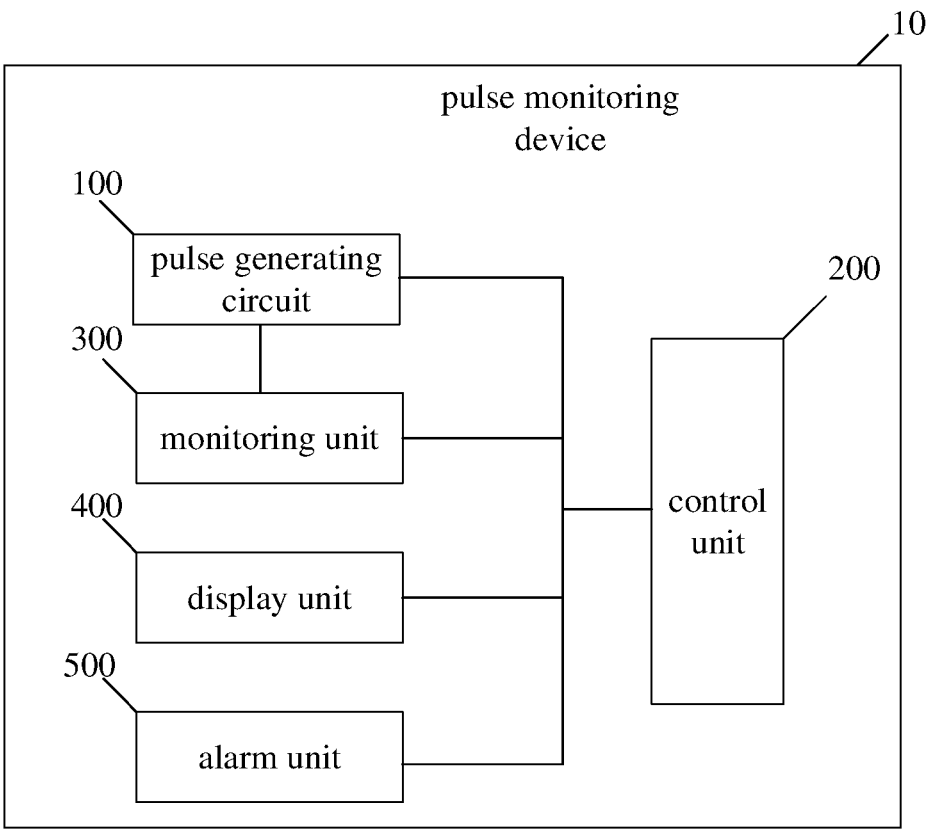
FIG. 2 is another schematic structural diagram of the pulse monitoring device according to the embodiments of the present application.

Optionally, as shown in FIG. 2, the pulse monitoring device 10 further includes a display unit 400 communicatively connected to the control unit 200 and configured to display a real-time impedance value.

Optionally, the display unit 400 is further configured to display a real-time impedance value curve, where the real-time impedance value curve comprises at least two real-time impedance values in a set time period, or, display the real-time impedance value and corresponding biological indicator information of the target biological tissue, where the biological indicator information comprises at least one of the following: heart rate, blood pressure or blood oxygen concentration.

Optionally, the display unit 400 may be a display screen, used to display such information as the real-time impedance value, the real-time impedance value curve, or biological indicator information.

Optionally, as shown in FIG. 2, the pulse monitoring device 10 further includes an alarm unit 500. The alarm unit 500 is communicatively connected to the control unit 200 and configured to issue an alarm prompt when the biological indicator information of the target biological tissue is greater than a set threshold. The alarm prompt includes emitting an alarm sound and/or outputting alarm information to the control unit 200. The control unit 200 is configured to output a termination instruction for the first pulse sequence in response to receiving the alarm information.

Figure 3:
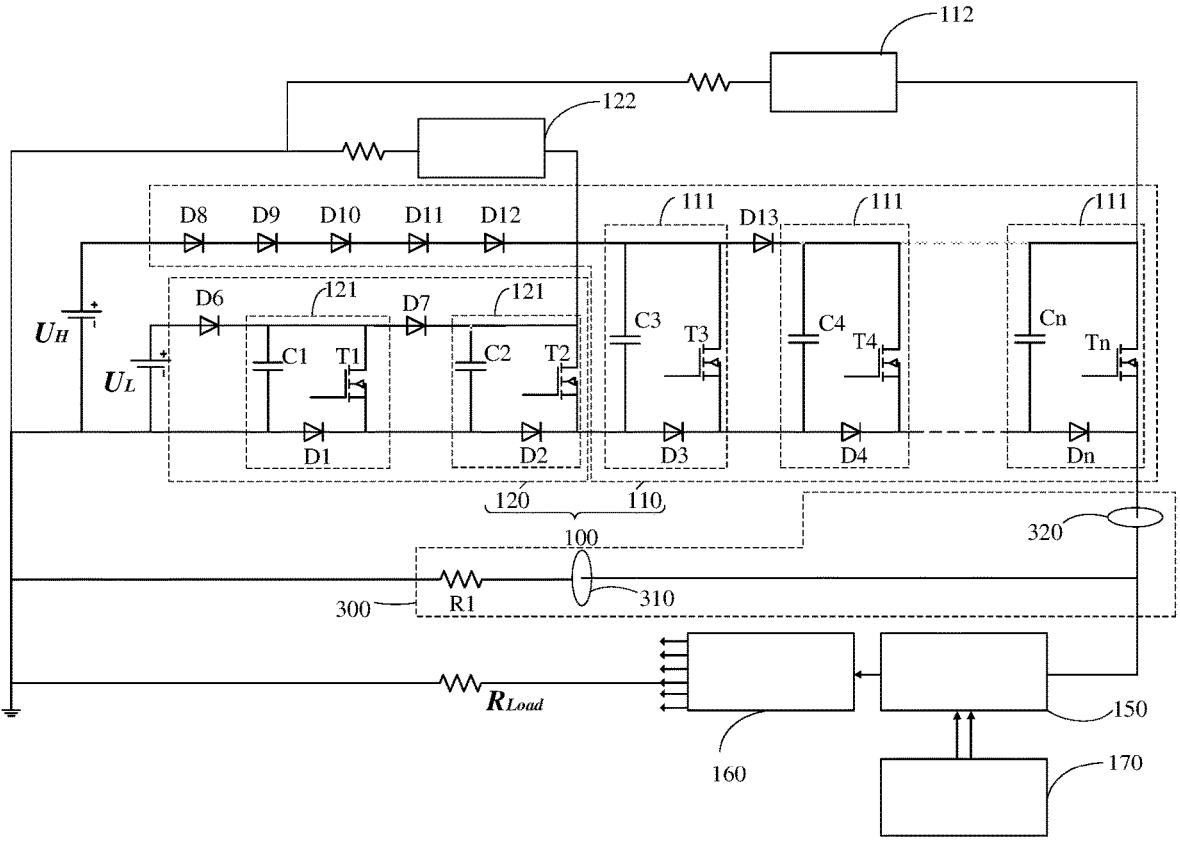
FIG. 3 is a schematic diagram of a circuit structure in the pulse monitoring device according to the embodiments of the present application.

In some embodiments, as shown in FIG. 3, the pulse generating circuit 100 includes a first pulse generating circuit 110 for outputting the first pulse sequence and a second pulse generating circuit 120 for outputting the second pulse sequence. The first pulse generating circuit 110 and the second pulse generating circuit 120 are integrated on a same circuit board.

In the embodiments of the present application, the first pulse generating circuit 110 and the second pulse generating circuit 120 are integrated on the same circuit board, so it allows a single circuit board to output the first pulse sequence and the second pulse sequence, accommodating both ablation and monitoring functionalities.

In some embodiments, as shown in FIG. 3, the first pulse generating circuit 110 includes at least one level of first pulse generating units 111 electrically connected sequentially.

Each first pulse generating unit 111 is electrically connected to the control unit 200, and configured to be turned on under control of the control unit 200 and apply the first pulse sequence to the target biological tissue.

Optionally, as shown in FIG. 3, each of the at least one level of first pulse generating units 111 includes a first capacitor, a first switching device and a first diode, a first terminal of the first capacitor is electrically connected to a first terminal of the first switching device, a positive electrode and a negative electrode of the first diode are electrically connected to a second terminal of the first capacitor and a second terminal of the first switching device respectively, and a control terminal of the first switching device is electrically connected to the control unit 200.

Optionally, when the first pulse generating circuit 110 discharges, the control unit 200 controls the first switching device of the first pulse generating unit 111 to be turned on.

Optionally, as shown in FIG. 3, the first pulse generating circuit 110 further includes at least one second diode; a first terminal of a first capacitor in a first level of first pulse generating unit 110 is electrically connected to a first power source UH through the at least one second diode. An anode of the second diode is electrically connected to the first power source UH, and a cathode of the second diode is electrically connected to the first terminal of the first capacitor in the first level of first pulse generating unit 110.

Optionally, as shown in FIG. 3, the first pulse generating circuit 110 further includes at least one third diode, an anode and a cathode of the third diode are electrically connected to two adjacent first pulse generating units 111 respectively. The anode and the cathode of the third diode are electrically connected to a first terminal of a first switching device in a previous level of first pulse generating unit and a first terminal of a first capacitor in a next level of first pulse generating unit.

In some embodiments, as shown in FIG. 3, the second pulse generating circuit 120 includes at least one level of second pulse generating units 121 electrically connected sequentially.

Each second pulse generating unit 121 is electrically connected to the control unit 200 and configured to be turned on under control of the control unit 200 and apply the second pulse sequence to the target biological tissue.

Optionally, as shown in FIG. 3, the second pulse generating unit 121 includes a second capacitor, a second switching device and a fourth diode. A first terminal of the second capacitor is electrically connected to a first terminal of the second switching device, a positive electrode and a negative electrode of the fourth diode are electrically connected to a second terminal of the second capacitor and a second terminal of the second switching device respectively, and a control terminal of the second switching device is electrically connected to the control unit 200.

Optionally, when the second pulse generating circuit 120 discharges, the control unit 200 controls the second switching device of the second pulse generating unit 121 to be turned on.

Optionally, the termination instruction for the first pulse sequence includes an instruction outputted by the control unit 200 to control the second switching device to be turned off.

Optionally, as shown in FIG. 3, the second pulse generating circuit 120 further includes at least one fifth diode. An anode of the fifth diode is electrically connected to a second power source UL, and a cathode of the fifth diode is electrically connected to a first terminal of a second capacitor in a first level of second pulse generating unit 121.

Optionally, as shown in FIG. 3, the second pulse generating circuit 120 further includes at least one sixth diode, an anode and a cathode of the sixth diode are electrically connected to two adjacent second pulse generating units 121 respectively. The anode and the cathode of the third diode are electrically connected to a first terminal of a second switching device in a previous level of second pulse generating unit and a first terminal of a second capacitor in a next level of second pulse generating unit.

Optionally, as shown in FIG. 3, the pulse monitoring device 10 further includes a first capacitor discharge relay 112 and a second capacitor discharge relay 122. First terminals of the first capacitor discharge relay 112 and the second capacitor discharge relay 122 are both grounded, second terminals of the first capacitor discharge relay 112 and the second capacitor discharge relay 122 are electrically connected to a last level of first pulse generating unit 111 and a last level of second pulse generating unit 121 respectively.

Through the first capacitor discharge relay 112 and the second capacitor discharge relay 122, it is able to manually control the capacitors to discharge in special circumstances where rapid discharge is required, so as to ensure the capacitors in the pulse generating circuit 100 to discharge in a more thorough and faster manner.

Optionally, as shown in FIG. 3, the pulse monitoring device 10 further includes a first output relay 150, a second output relay 160 and a foot switch 170. A first terminal of the first output relay 150 is electrically connected to the first pulse generating circuit 110, the second pulse generating circuit 120, a second terminal of the first output relay 150 is electrically connected to a first terminal of the second output relay 160, and a second terminal of the second output relay 160 is electrically connected to a load Rload which is grounded. The foot switch 170 is electrically connected to a third terminal of the first output relay 150 and configured to control the load RLoad, the first output relay 150 and the first pulse generating circuit 110 or the second pulse generating circuit 120 to form a discharge circuit.

Through the first output relay 150, the second output relay 160 and the foot switch 170, it is able to enable a power supply circuit where the load RLoad (i.e., a human body part) is located to be opened, thereby improving safety. The second output relay 160 may be a 12-channel relay. The load RLoad is considered as an equivalent load of the target biological tissue.

Optionally, as shown in FIG. 3, the monitoring unit 300 includes a first Pearson coil 310, a second Pearson coil 320 and a first resistor R1. A first terminal of the first Pearson coil 310 is connected to the first resistor R1, the first resistor R1 is grounded, a second terminal of the first Pearson coil 310 is connected to a first terminal of the second Pearson coil 320, and a second terminal of the second Pearson coil 320 is electrically connected to the first pulse generating circuit 110 and the second pulse generating circuit 110. The feedback circuit is a circuit formed by the second pulse generating circuit 120 and the load RLoad.

Optionally, the first Pearson coil 310 has following functions. Firstly, it functions as a discharge channel for the pulses generated when the discharge circuit is not discharging. Secondly, a resistance of the first Pearson coil approximately ranges from 10 kΩ to 100 kΩ, it may be used for real-time voltage monitoring. The second Pearson coil 320 is used to measure current.

Optionally, when the second pulse generating circuit 120 is electrically connected to the load RLoad to form the feedback circuit, the first Pearson coil 310 and the second Pearson coil 320 serve as two sampling points for collecting real-time voltage and real-time current on the feedback circuit.

As an example, FIG. 3 shows a schematic diagram of the electrical connection between the pulse generation circuit 100 and the power source, the load RLoad as well as the monitoring unit. A power supply circuit where the first power source UH is located is a high-voltage nanosecond pulse generation circuit. A power supply circuit where the second power source UL is located is a low-voltage microsecond pulse generating circuit, and serves as a feedback circuit. The power supply circuit where the second power supply UL is located includes two levels of second pulse generating units 121, and outputs a voltage with an amplitude ranging from 0 to 500V. The power supply circuit where the first power supply UH is located may include twenty levels of first pulse generating units 111, and is capable of generating a high-voltage nanosecond pulse ranging from 0 to 15 kV.

Optionally, in this embodiment, in the low-voltage microsecond pulse generating circuit, a capacitor C1, a switching device T1 and a diode D1 form one second pulse generating unit 121, and a capacitor C2, a switching device T2 and a diode D2 form another one second pulse generating unit 121. A diode D7 serves as the sixth diode, and a diode D6 serves as the fifth diode.

Optionally, in this embodiment, in the high-voltage nanosecond pulse generating circuit, a capacitor C3, a switching device T3 and a diode D3 form one first pulse generating unit 111, a capacitor C4, a switching device T4 and a diode D4 form another one first pulse generating unit 111, and a capacitor Cn, a switching device Tn and a diode Dn form yet another one first pulse generating unit 111. A diode D8, a diode D9, a diode D10, a diode D11 and a diode D12 are each the second diode, the diode D9, the diode D10, the diode D11 and the diode D12 are connected in series sequentially, and a diode D13 is the third diode.

Optionally, the switching device used in the low-voltage microsecond pulse generating circuit is a Metal-Oxide-Semiconductor Field-Effect Transistor (MOSFET), and the switching device used in the high-voltage nanosecond pulse generating circuit is an Insulated Gate Bipolar Transistor (IGBT).

Based on the same inventive concept, the embodiments of the present application provide a pulse monitoring method. As shown in FIG. 3, the pulse monitoring method includes steps S401 to S404.

S401, applying a first pulse sequence and a second pulse sequence to target biological tissue, where a voltage of the second pulse sequence is smaller than a voltage of the first pulse sequence, and the first pulse sequence is used to ablate the target biological tissue.

In the embodiments of the present application, the second pulse sequence applied to the target biological tissue is used to reflect the status of the target biological tissue in real time and monitor the ablation status of the target biological tissue during the pulse ablation process, thereby guiding the pulse ablation process according to the ablation status of the target biological tissue.

Optionally, the pulse generating circuit 100 applies the first pulse sequence and the second pulse sequence to the target biological tissue.

In some embodiments of the present application, applying the first pulse sequence and the second pulse sequence to the target biological tissue includes applying a first set quantity of first pulse sequences and a second set quantity of second pulse sequences to the target biological tissue sequentially and alternately.

Optionally, the pulse generating circuit 100 sequentially and alternately applies the first set quantity of first pulse sequences and the second set quantity of second pulse sequences to the target biological tissue.

Optionally, the first set quantity and the second set quantity are the same or different. For example, when the first set quantity and the second set quantity are both 1, one first pulse sequence and one second pulse sequence are applied alternately. For another example, the first set quantity is 3, and the second set quantity is 1. After applying 3 first pulse sequences, 1 second pulse sequence is applied, which are performed in a repeated cycle.

In the embodiments of the present application, it is able to alternately apply the first pulse sequence and the second pulse sequence, so that the second pulse sequence is applied in each period, and the ablation status of the target biological tissue is monitored in real time, thereby to make an immediate response to the changes in the target biological tissue.

In some embodiments of the present application, the first pulse sequence includes at least one type of pulse and the second pulse sequence comprises at least one type of pulse.

Optionally, the first pulse sequence has only one type of pulse, and the second pulse sequence has only one type of pulse, and a voltage of the pulse in the first pulse sequence is higher than a voltage of the pulse in the second pulse sequence.

In some embodiments of the present application, the first pulse sequence includes a nanosecond pulse, or the first pulse sequence includes a nanosecond pulse and a microsecond pulse. The second pulse sequence includes a microsecond pulse.

Optionally, the first pulse sequence includes a nanosecond pulse and a microsecond pulse, and the microsecond pulse is also used to ablate the target biological tissue.

In some embodiments of the present application, the voltage of the first pulse sequence is greater than 500V and not greater than 15 kV; and/or, the voltage of the second pulse sequence is not greater than 500V.

Figure 5:
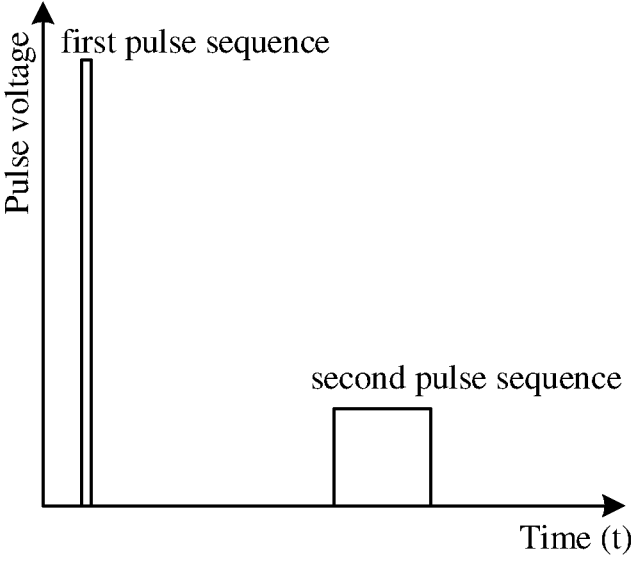
FIG. 5 is a waveform diagram of an outputted pulse sequence according to the embodiments of the present application.

As an example, refer to FIG. 5, where the horizontal axis represents time and the vertical axis represents pulse voltage. A first pulse sequence is a high-voltage nanosecond pulse, a second pulse sequence is a low-voltage microsecond pulse, and the high-voltage nanosecond pulse and the low-voltage microsecond pulse are applied alternately. The high-voltage nanosecond pulse is used to ablate the target biological tissue, and the low-voltage microsecond pulse is used to monitor the ablation status of the target biological tissue.

Optionally, a current range of the high-voltage nanosecond pulse is 0 to 300 A, and a pulse duration of the high-voltage nanosecond pulse is 200 nanoseconds to 1000 nanoseconds. A current range of the low-voltage microsecond pulse is 0 to 100 A, and a pulse duration of the low-voltage microsecond pulse is 10 microseconds to 300 microseconds.

S402, obtaining a feedback signal after the second pulse sequence is applied to the target biological tissue.

Optionally, the monitoring unit 300 obtains the feedback signal after the second pulse sequence is applied to the target biological tissue, and outputs the feedback signal to the control unit 200.

In some embodiments of the present application, obtaining the feedback signal after the second pulse sequence is applied to the target biological tissue includes: obtaining a real-time voltage and a real-time current of a feedback circuit corresponding to the target biological tissue after the second pulse sequence is applied to the target biological tissue.

S403, determining, according to the feedback signal, whether a termination condition for the first pulse sequence is met.

Optionally, the monitoring unit 300 outputs the feedback signal to the control unit 200, and the control unit 200 determines whether the termination condition for the first pulse sequence is met based on the feedback signal.

Through research, it has been found that, in the biological tissue, where cells are neatly and densely arranged, a single cell may be regarded as a basic structural unit with a specific impedance. Following the ablation with the high-voltage nanosecond pulse, some cells rupture, inevitably leading to changes in the impedance between two electrodes. Generally, the higher the degree of tissue ablation, the lower the impedance value. Therefore, the impedance may reflect the extent of tissue ablation to a certain degree.

Based on the aforementioned considerations, in some embodiments, determining whether the termination condition for the first pulse sequence is met according to the feedback signal includes:

determining, according to the real-time voltage and real-time current of the feedback circuit, a real-time impedance value of the target biological tissue;

determining whether the real-time impedance value is less than a set impedance value; or, displaying the real-time impedance value and determining whether a termination instruction for the first pulse sequence is received.

In some embodiments, determining whether the termination condition for the first pulse sequence is met according to the feedback signal includes:

determining, by the control unit 200, a real-time impedance value of the target biological tissue according to the real-time voltage and real-time current of the feedback circuit;

determining, by the control unit 200, whether the real-time impedance value is less than a set impedance value; or, displaying, by the display unit 400, the real-time impedance value and determining, by the control unit 200, whether a termination instruction for the first pulse sequence is received.

Optionally, the set impedance value is a value obtained by medical personnel based on ablation tests. When the real-time impedance value is less than the set impedance value, it is determined that an ablation expectation has been met.

Optionally, the process for calculating the real-time impedance value is shown in Equation (1):

$$Z = \frac{U_{in}}{I_m} \qquad \text{Equation (1)}$$

Uin represents a real-time voltage of the input pulse, Im denotes a real-time current, and Z is a calculated real-time impedance value. The calculated real-time impedance value serves as the equivalent impedance of the target biological tissue, which may accurately reflect the ablation status of the target biological tissue.

In some embodiments of the present application, displaying the real-time impedance value includes displaying a real-time impedance value curve, where the real-time impedance value curve includes at least two real-time impedance values in a set time period.

Optionally, displaying the real-time impedance value includes: displaying, by the display unit 400, a real-time impedance value curve, where the real-time impedance value curve includes at least two real-time impedance values in a set time period.

Optionally, the real-time impedance value is displayed to facilitate a doctor to determine whether to stop applying the first pulse sequence for ablation based on the real-time impedance value. In practical applications, the doctor may determine, based on experiences in combination with a current condition of the biological tissue, whether the ablation should continue or be terminated. When the real-time impedance value is displayed, it makes the entire medical process form a closed loop, and the doctor's decision-making can be based on evidence, so as to improve the ablation effect.

Optionally, displaying the real-time impedance value includes: displaying the real-time impedance value and corresponding biological indicator information of the target biological tissue, where the biological indicator information comprises at least one of the following: heart rate, blood pressure or blood oxygen concentration.

Optionally, displaying the real-time impedance value includes: displaying, by the display unit 400, the real-time impedance value and corresponding biological indicator information of the target biological tissue, where the biological indicator information comprises at least one of the following: heart rate, blood pressure or blood oxygen concentration.

Optionally, displaying the real-time impedance value and determining whether the termination instruction for the first pulse sequence is received includes: issuing an alarm prompt when the biological indicator information of the target biological tissue is greater than a set threshold, where the alarm prompt includes emitting an alarm sound and/or outputting alarm information. When receiving the alarm information, the control unit 200 outputs the termination instruction for the first pulse sequence.

Optionally, displaying the real-time impedance value and determining whether the termination instruction for the first pulse sequence is received includes: issuing, by the alarm unit 500, an alarm prompt when the biological indicator information of the target biological tissue is greater than a set threshold.

In the embodiments of the present application, it is able to simultaneously monitor the patient's biometric information while ablating the target biological tissue, so as to avoid the occurrence of danger during the ablation process of the patient, thereby to further ensure the ablation effect.

S404, stopping applying the first pulse sequence when it is determined that the termination condition for the first pulse sequence is met.

Optionally, stopping applying the first pulse sequence by the control unit 200 when it is determined that the termination condition for the first pulse sequence is met includes: stopping applying the first pulse sequence when it is determined that the real-time impedance value is less than the set impedance value; or, stopping applying the first pulse sequence when it is determined that the termination instruction for the first pulse sequence is received.

Optionally, stopping applying the first pulse sequence when it is determined that the termination instruction for the first pulse sequence is received includes: outputting, by the control unit 200, the termination instruction for the first pulse sequence to the pulse generating circuit 100 when determining that the real-time impedance value is less than the design impedance value, and controlling the pulse generating circuit 100 to stop applying the first pulse sequence; or, controlling, by the control unit 200, the pulse generating circuit 100 to stop applying the first pulse sequence when determining that the termination instruction for the first pulse sequence is received.

Optionally, when it is determined that the real-time impedance value is not less than the set impedance value, applying the first pulse sequence for ablation continues until the real-time impedance value is less than the set impedance value. When it is determined that the real-time impedance value is less than the set impedance value, it indicates that the ablation expectation is achieved, and it may continue to apply the first pulse sequence to ablate the target biological tissue.

In the above technical solutions of the embodiments of the present application, the target biological tissue is considered as an electrical network, the second pulse sequence is applied to the target biological tissue, and a response of the target biological tissue to this stimulus can be measured in the feedback circuit. Based on the stimulus and response, the equivalent real-time impedance value of the biological tissue can be determined, and the pulse ablation effect can be evaluated based on the real-time impedance value.

In the embodiments of the present application, it is able to calculate the real-time impedance value of the target biological tissue based on the real-time voltage and the real-time current, and based on whether a single pulse ablation, as indicated by the real-time impedance value, reaches the expected degree of tissue ablation, so as to guide medical personnel in the pulse ablation process.

Figure 6:
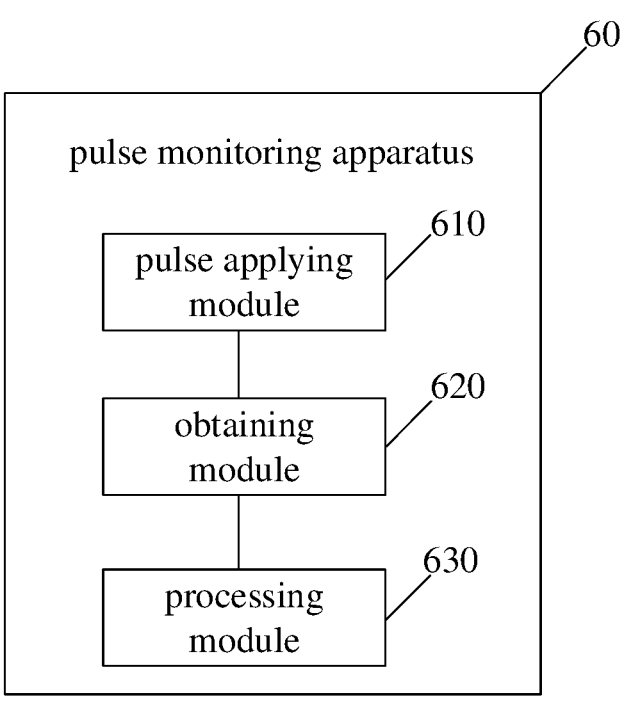
FIG. 6 is a schematic diagram of a pulse monitoring apparatus according to the embodiments of the present application.

Based on the same inventive concept, the embodiments of the present application provide a pulse monitoring apparatus. As shown in FIG. 6, the pulse monitoring apparatus 60 includes a pulse applying module 610, an obtaining module 620 and a processing module 630.

The pulse applying module 610 is configured to apply a first pulse sequence and a second pulse sequence to target biological tissue, where a voltage of the second pulse sequence is smaller than a voltage of the first pulse sequence, and the first pulse sequence is used to ablate the target biological tissue.

The obtaining module 620 is configured to obtain a feedback signal after the second pulse sequence is applied to the target biological tissue.

The processing module 630 is configured to determine, according to the feedback signal, whether a termination condition for the first pulse sequence is met, and stop applying the first pulse sequence when it is determined that the termination condition for the first pulse sequence is met.

Optionally, the pulse applying module 610 is further configured to apply a first set quantity of first pulse sequences and a second set quantity of second pulse sequences to the target biological tissue sequentially and alternately.

Optionally, the obtaining module 620 is further configured to obtain a real-time voltage and a real-time current of a feedback circuit corresponding to the target biological tissue after the second pulse sequence is applied to the target biological tissue.

Optionally, the processing module 630 is further configured to determine, according to the real-time voltage and real-time current of the feedback circuit, a real-time impedance value of the target biological tissue; determine whether the real-time impedance value is less than a set impedance value; or, display the real-time impedance value and determine whether a termination instruction for the first pulse sequence is received.

Optionally, the processing module 630 is further configured to display a real-time impedance value curve, where the real-time impedance value curve includes at least two real-time impedance values in a set time period, or, display the real-time impedance value and corresponding biological indicator information of the target biological tissue, where the biological indicator information includes at least one of the following: heart rate, blood pressure or blood oxygen concentration.

Optionally, the processing module 630 is further configured to stop applying the first pulse sequence when it is determined that the real-time impedance value is less than the set impedance value, or, stop applying the first pulse sequence when it is determined that the termination instruction for the first pulse sequence is received.

Based on the same inventive concept, the embodiments of the present application provide a computer-readable storage medium having a computer program stored thereon, the computer program implements, when executed by the pulse monitoring device 10, the pulse monitoring method in any embodiment of the present application.

The computer-readable medium in the embodiments of the present application may be a computer-readable signal medium or a computer-readable storage medium, or any combination thereof. The computer-readable storage medium may be, for example, but not limited to, an electronic, magnetic, optical, electromagnetic, infrared, or semiconductor system, apparatus or device, or any combination thereof. In more specific examples, the computer readable storage medium may include, but not limited to, an electrical connection having one or more wires, a portable computer disk, a hard drive, a random access memory (RAM), a read only memory (ROM), a removable programmable read-only memory (EPROM or flash memory), an optical fiber, a portable compact disk read-only memory (CD-ROM), an optical storage device, a magnetic storage device, or any suitable combination thereof.

The computer-readable medium in the embodiments of the present application may be any tangible medium containing or storing a program, and the program may be used by or in combination with an instruction execution system, apparatus or device. In the present application, the computer-readable signal medium may include a data signal in baseband or propagated as part of a carrier wave, in which computer-readable program code is carried. The propagated data signal may take many forms, including but not limited to an electromagnetic signal, an optical signal, or any suitable combination thereof. The computer-readable signal medium may also be any computer-readable medium other than the computer-readable storage medium that can send, propagate, or transmit a program used by or in connection with an instruction execution system, apparatus, or device. Program code on the computer-readable medium may be transmitted by using any suitable medium, including but not limited to: wire, optical fiber cable, radio frequency (RF), etc., or any suitable combination thereof.

When the embodiments of the present application are implemented, at least the following beneficial effects can be achieved.

Firstly, in the pulse monitoring method of the embodiments of the present application, during the pulse ablation process, it is able to determine an ablation status of the target biological tissue based on the feedback signal, so as to monitor the ablation status of the target biological tissue during the pulse ablation process in real time. When it is determined that a termination condition for the first pulse sequence is met, the output of the first pulse sequence is stopped. That is, in the embodiments of the present application, it is able to guide the pulse ablation process according to changes in the biological tissue. After determining that the pulse ablation effect is achieved, the output of the first pulse sequence for ablating the biological tissue is stopped, thereby to guide the pulse ablation process according to the changes in the target biological tissue.

Secondly, in the embodiments of the present application, it is able to alternately apply the first pulse sequence and the second pulse sequence, so that the second pulse sequence is applied in each period, and the ablation status of the target biological tissue is monitored in real time, thereby to make an immediate response to the changes in the target biological tissue.

Thirdly, in the embodiments of the present application, it is able to simultaneously monitor the patient's biometric information while ablating the target biological tissue, so as to avoid the occurrence of danger during the ablation process of the patient, thereby to further ensure the ablation effect.

Fourthly, in the embodiments of the present application, it is able to calculate the real-time impedance value of the target biological tissue based on the real-time voltage and the real-time current, and based on whether a single pulse ablation, as indicated by the real-time impedance value, reaches the expected degree of tissue ablation, so as to guide medical personnel in the pulse ablation process.

Fifthly, in the embodiments of the present application, the first pulse generating circuit 110 and the second pulse generating circuit 120 are integrated on the same circuit board, so it allows a single circuit board to output the first pulse sequence and the second pulse sequence, accommodating both ablation and monitoring functionalities.

Lastly, through the pulse monitoring device 10 in the embodiments of the present application, it realizes that two functions of pulse ablation and monitoring are integrated into one device, and thereby it does not need to be equipped with other monitoring devices or independent modules, making it convenient to use and operate.

As can be appreciated by a person skilled in the art, steps, measures and schemes in various operations, methods and processes that have already been discussed in the embodiments of the present application may be replaced, modified, combined or deleted. In a possible embodiment of the present disclosure, the other steps, measures and schemes in various operations, methods and processes that have already been discussed in the embodiments of the present application may also be replaced, modified, rearranged, decomposed, combined or deleted. In another possible embodiment of the present application, steps, measures and schemes in various operations, methods and processes that are known in the related art and have already been discussed in the embodiments of the present application may also be replaced, modified, rearranged, decomposed, combined or deleted.

Such words as "first" and "second" are merely for illustrative purposes, rather than to implicitly or explicitly indicate the number of the defined technical features. In this regard, the technical features defined with such words as "first" and "second" may implicitly or explicitly include one or more technical features. Further, such a phrase as "a plurality of" is used to indicate that there are at least two, e.g., two or three, components, unless otherwise specified.

It should be further appreciated that, although with arrows, the steps in the flow charts may not be necessarily performed in an order indicated by the arrows. Unless otherwise defined, the order of the steps may not be strictly defined, i.e., the steps may also be performed in another order. In addition, each of at least parts of the steps in the flow charts may include a plurality of sub-steps or stages, and these sub-steps or stages may not be necessarily performed at the same time, i.e., they may also be performed at different times. Furthermore, these sub-steps or stages may not be necessarily performed sequentially, and instead, they may be performed alternately with the other steps or at least parts of sub-steps or stages of the other steps.

The above embodiments are partial embodiments of the present application, it should be appreciated that those skilled in the art may make various improvements and modifications without departing from the principle of the present disclosure, and theses improvement and modifications shall fall within the scope of the present disclosure.

What is claimed is:

1. A pulse monitoring device, comprising: a pulse generating circuit, a control unit, a monitoring unit and a display unit; wherein, the control unit is communicatively connected to the pulse generating circuit, and configured to control the pulse generating circuit to apply a first pulse sequence and a second pulse sequence to target biological tissue sequentially and alternately in a plurality of periods; wherein the second pulse sequence is applied in each period; a voltage of the second pulse sequence is smaller than a voltage of the first pulse sequence, and the first pulse sequence is used to ablate the target biological tissue;

the control unit is further configured to determine, according to a feedback signal forwarded by the monitoring unit, whether a termination condition for the first pulse sequence is met, and output a termination instruction for the first pulse sequence to the pulse generating circuit when it is determined that the termination condition for the first pulse sequence is met; and the monitoring unit is communicatively connected to the control unit, and configured to obtain the feedback signal after the second pulse sequence is applied to the target biological tissue, and output the feedback signal to the control unit;

the pulse generating circuit is configured to stop applying the first pulse sequence when it is determined that the termination condition for the first pulse sequence is met;

the monitoring unit is further configured to obtain a real-time voltage and a real-time current of a feedback circuit corresponding to the target biological tissue after the second pulse sequence is applied to the target biological tissue;

the control unit is further configured to:

determine, according to the real-time voltage and real-time current of the feedback circuit, a real-time impedance value of the target biological tissue; and determine whether the real-time impedance value is less than a set impedance value; or, display through the display unit the real-time impedance value and determine whether the termination instruction for the first pulse sequence is received; and the control unit is further configured to:

stop applying the first pulse sequence when it is determined that the real-time impedance value is less than the set impedance value; or, stop applying the first pulse sequence when it is determined that the termination instruction for the first pulse sequence is received;

the pulse generating circuit comprises a first pulse generating circuit for outputting the first pulse sequence and a second pulse generating circuit for outputting the second pulse sequence;

the first pulse generating circuit and the second pulse generating circuit are integrated on a same circuit board;

the first pulse generating circuit comprises at least one level of first pulse generating units electrically connected sequentially;

each first pulse generating unit is electrically connected to the control unit, and configured to be turned on under control of the control unit and apply the first pulse sequence to the target biological tissue;

each of the at least one level of first pulse generating units comprises a first capacitor, a first switching device and a first diode, a first terminal of the first capacitor is electrically connected to a first terminal of the first switching device, a positive electrode and a negative electrode of the first diode are electrically connected to a second terminal of the first capacitor and a second terminal of the first switching device respectively, and a control terminal of the first switching device is electrically connected to the control unit.

2. The pulse monitoring device according to claim 1, wherein the first pulse generating circuit further comprises at least one second diode; a first terminal of a first capacitor in a first level of first pulse generating unit in the at least one level of first pulse generating units is electrically connected to a first power source through the at least one second diode.

3. The pulse monitoring device according to claim 1, wherein the first pulse generating circuit further comprises at least one third diode, an anode and a cathode of the third diode are electrically connected to two adjacent first pulse generating units respectively.

4. The pulse monitoring device according to claim 1, wherein the second pulse generating circuit comprises at least one level of second pulse generating units electrically connected sequentially;

wherein each second pulse generating unit is electrically connected to the control unit and configured to be turned on under control of the control unit and apply the second pulse sequence to the target biological tissue.

5. The pulse monitoring device according to claim 4, wherein the second pulse generating unit comprises a second capacitor, a second switching device and a fourth diode; a first terminal of the second capacitor is electrically connected to a first terminal of the second switching device, a positive electrode and a negative electrode of the fourth diode are electrically connected to a second terminal of the second capacitor and a second terminal of the second switching device respectively, and a control terminal of the second switching device is electrically connected to the control unit.

6. The pulse monitoring device according to claim 1, wherein the pulse monitoring device further comprises a display unit communicatively connected to the control unit, wherein the display unit is configured to display at least one of a real-time impedance value, a real-time impedance value curve or biological indicator information.

7. The pulse monitoring device according to claim 1, wherein the pulse monitoring device further comprises an alarm unit communicatively connected to the control unit, wherein the alarm unit is configured to issue an alarm prompt when the biological indicator information of the target biological tissue is greater than a set threshold.

8. The pulse monitoring device according to claim 1, wherein the pulse generating circuit is configured to apply a first set quantity of first pulse sequences and a second set quantity of second pulse sequences to the target biological tissue sequentially and alternately.

9. The pulse monitoring device according to claim 1, wherein the first pulse sequence comprises at least one type of pulse and the second pulse sequence comprises at least one type of pulse.

10. The pulse monitoring device according to claim 1, wherein the first pulse sequence comprises a nanosecond pulse, or the first pulse sequence comprises a nanosecond pulse and a microsecond pulse;

the second pulse sequence comprises a microsecond pulse.

11. The pulse monitoring device according to claim 10, wherein the voltage of the first pulse sequence is greater than 500 V and not greater than 15 kV.

12. The pulse monitoring device according to claim 10, wherein the voltage of the second pulse sequence is not greater than 500 V.

13. The pulse monitoring device according to claim 1, wherein the display unit is further configured to perform at least one of the following:

displaying a real-time impedance value curve, wherein the real-time impedance value curve comprises at least two real-time impedance values in a set time period; or, displaying the real-time impedance value and corresponding biological indicator information of the target biological tissue; wherein the biological indicator information comprises at least one of the following: heart rate, blood pressure or blood oxygen concentration.

14. The pulse monitoring device according to claim 1, further comprising an alarm unit communicatively connected to the control unit, wherein the alarm unit is configured to issue an alarm prompt when the biological indicator information of the target biological tissue is greater than a set threshold; the alarm prompt comprises at least one of the following: emitting an alarm sound or outputting alarm information;

the control unit is further configured to output the termination instruction for the first pulse sequence in response to receiving the alarm information.

* * * * *